(12) United States Patent
Beretta et al.

(10) Patent No.: US 10,405,897 B2
(45) Date of Patent: Sep. 10, 2019

(54) FIXING DEVICE FOR A SURGICAL ANCHOR MEMBER

(71) Applicant: MEDACTA INTERNATIONAL SA, Castel San Pietro (CH)

(72) Inventors: Daniele Beretta, Maslianico (IT); Meinrad Fiechter, Lugano (CH); Francesco Siccardi, Sonvico (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 374 days.

(21) Appl. No.: 15/302,004

(22) PCT Filed: Apr. 3, 2015

(86) PCT No.: PCT/IB2015/052459
§ 371 (c)(1),
(2) Date: Oct. 5, 2016

(87) PCT Pub. No.: WO2015/155658
PCT Pub. Date: Oct. 15, 2015

(65) Prior Publication Data
US 2017/0181776 A1    Jun. 29, 2017

(30) Foreign Application Priority Data

Apr. 8, 2014  (IT) ............................... MI2014A0649

(51) Int. Cl.
*A61B 17/70*       (2006.01)
*A61B 17/88*       (2006.01)

(52) U.S. Cl.
CPC ...... *A61B 17/7091* (2013.01); *A61B 17/7032* (2013.01); *A61B 17/7037* (2013.01); *A61B 17/7049* (2013.01); *A61B 17/7076* (2013.01); *A61B 17/8875* (2013.01)

(58) Field of Classification Search
CPC .................................................. A61B 17/7091
See application file for complete search history.

(56) References Cited

U.S. PATENT DOCUMENTS

| | | | |
|---|---|---|---|
| 7,722,623 B2 | 5/2010 | Franks et al. | |
| 8,460,308 B2 | 6/2013 | Marino et al. | |
| 8,608,746 B2 * | 12/2013 | Kolb | A61B 17/7076 606/86 A |
| 2008/0051794 A1 | 2/2008 | Dec et al. | |
| 2013/0023941 A1 | 1/2013 | Jackson et al. | |

(Continued)

FOREIGN PATENT DOCUMENTS

JP       2013078576 A     5/2013

OTHER PUBLICATIONS

JP Office Action for JP2016561684, dated Nov. 13, 2018, 4 pages.

*Primary Examiner* — Andrew Yang
(74) *Attorney, Agent, or Firm* — Ference & Associates LLC

(57) ABSTRACT

A fixing device is for a surgical anchor member. The fixing device may include a control component joined to a connecting portion, which is in turn connected to a shaft provided at one end with coupling units for connecting the fixing device to a fastening element suitable to couple with a respective fastening seat of a surgical anchor element. The fixing device may include a centering component for the coupling of the fastening member with the respective fastening seat of the surgical anchor member.

11 Claims, 16 Drawing Sheets

(56) References Cited

U.S. PATENT DOCUMENTS

2013/0030477 A1 1/2013 Matthis et al.
2013/0066386 A1 3/2013 Biedermann et al.
2013/0085536 A1 4/2013 Biedermann et al.
2014/0163625 A1 6/2014 Meyer et al.

* cited by examiner

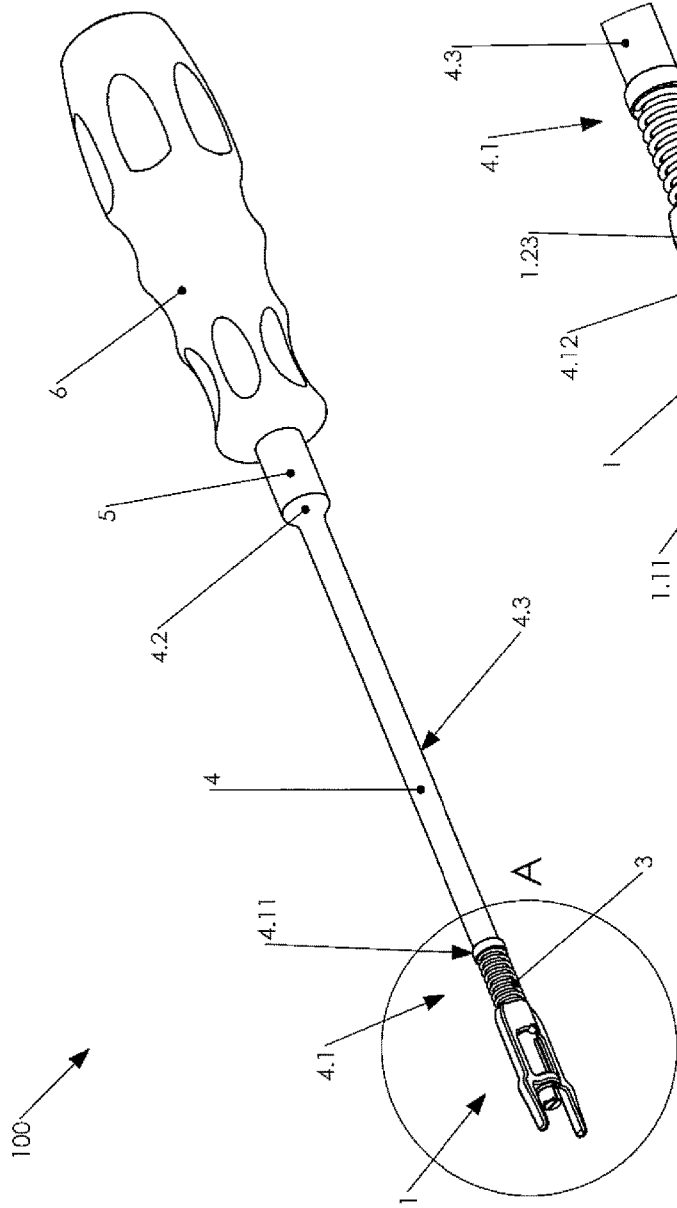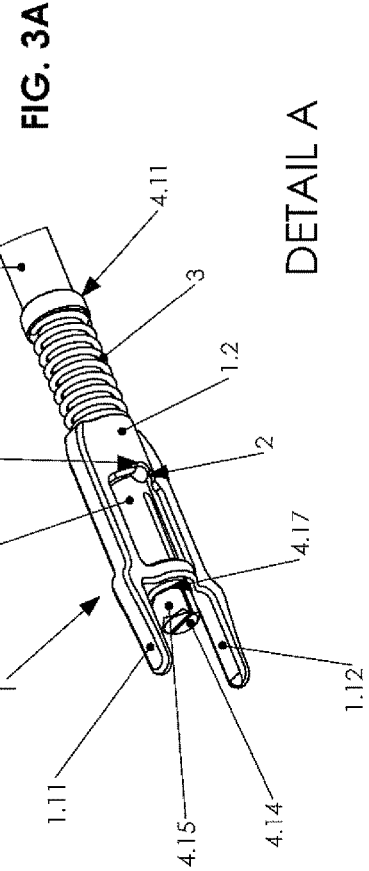

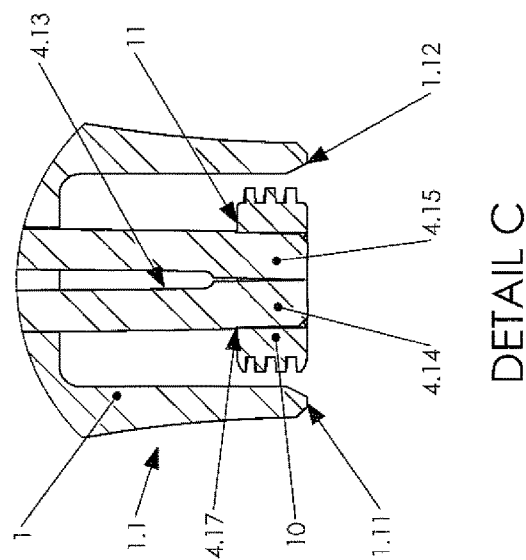
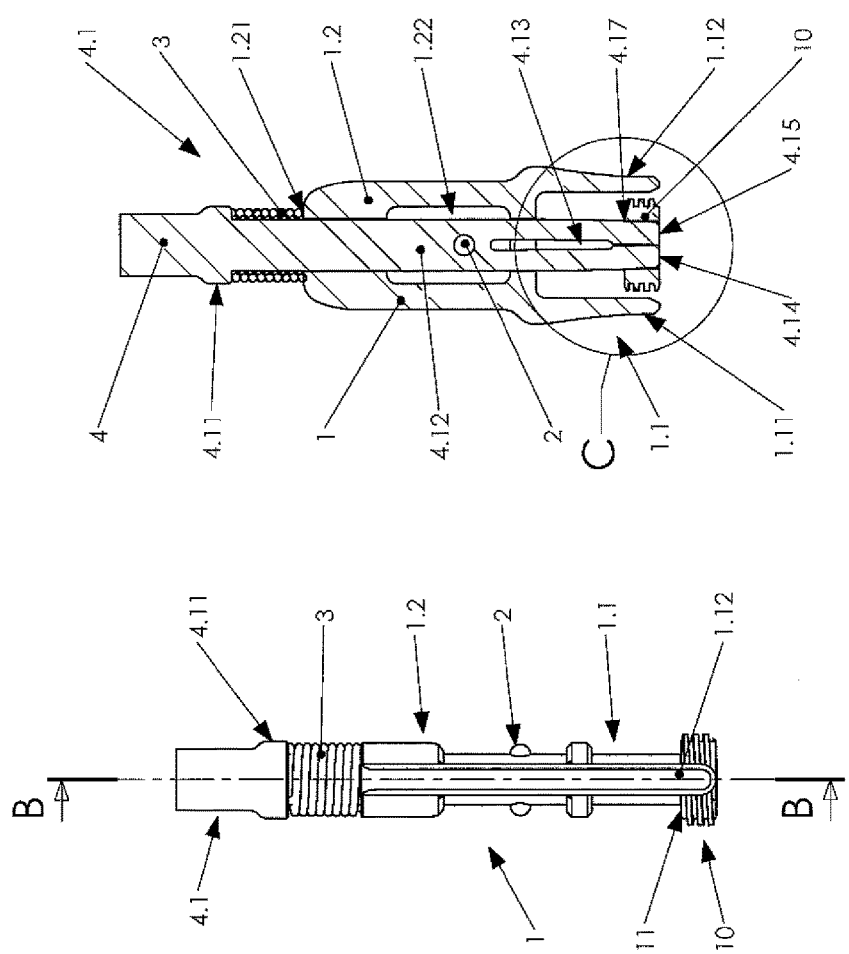
FIG. 5C
FIG. 5B
FIG. 5A

DETAIL E

SECTION F-F

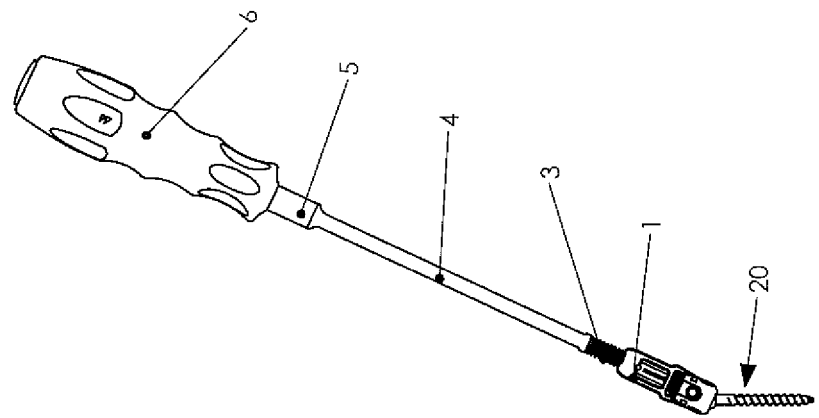
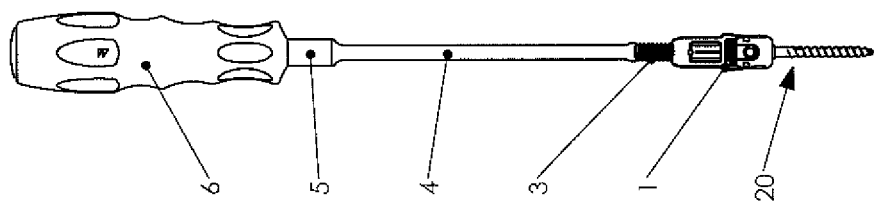
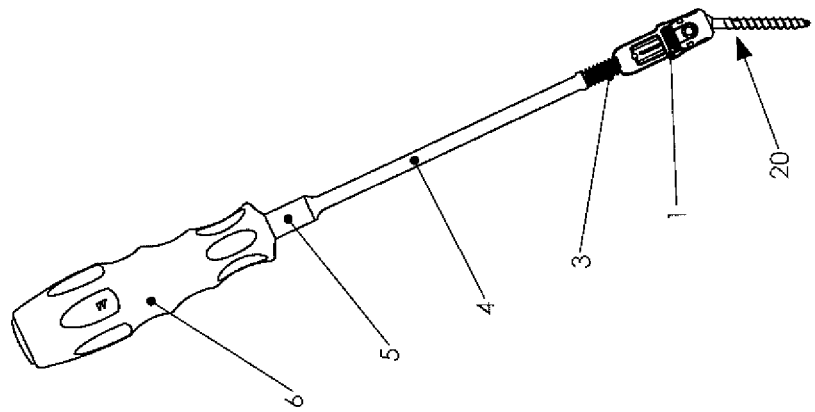
FIG. 10

SECTION H-H

FIXING DEVICE FOR A SURGICAL ANCHOR MEMBER

RELATED APPLICATION

This application is based upon prior filed copending International Application No. PCT/IB2015/052459 filed Apr. 3, 2015, which claims priority to Italian Application No. MI2014A000649, filed Apr. 8, 2014, the entire subject matter of these applications is incorporated herein by reference in its entirety.

TECHNICAL FIELD

The present disclosure is directed to a medical device, and more particularly, to a device for operating on spine disorders and related methods.

BACKGROUND

Operations on these types of characteristic problems of the spine frequently require the stabilization of a portion of the spinal tract so as to facilitate the fusion of two or more vertebrae into a single bone structure. This type of operation is frequently used for the correction of many pathological conditions of the vertebral column such as, for example, degenerative disc diseases, scoliosis, spinal stenosis or the like.

The stabilization of the vertebral column allows bone tissue to be created in the intervertebral area. In this way, part of the vertebral column is fused into a single bone structure. The stabilization of the vertebral column has been studied in the past and various methods and devices have been developed for the correction of many characteristic diseases of this part of the body, in order to stabilize its configuration, facilitating vertebral fusion at various levels.

One of these known systems envisions a corrective bar being arranged longitudinally along the spinal tract that requires surgery. This corrective bar is conformed so as to restore the correct anatomical shape, which is peculiar to that specific tract of a healthy vertebral column.

Therefore, with this method, the corrective bar is positioned along the vertebral column to engage various vertebrae, according to requirements. It should be noted that, typically, in this type of surgery two parallel corrective bars are arranged to the rear of the sides of the central area of the patient's vertebral column. Therefore, during the surgery, the pair of corrective bars is fixed to the vertebral column through various anchoring means including, for example, screws. The screws are fixed to the bone structure, typically to the vertebral peduncle.

The inclination of the corrective bar and, consequently, the positioning of the set screws, vary according to the type of correction to be made and, naturally, vary from vertebra to vertebra. One type of screws known in the state of the art that are widely used in the application are polyaxial screws. Here, the head of the screw can vary its angulation with respect to the threaded stem for better adaptation to the surgical requirements until a set screw is coupled to it.

It appears clear how it is fundamental, for a successful operation, to correctly fix both the corrective bar and the screws to which it will be fixed. In fact, the corrective bar is inserted into a head of the polyaxial screw and secured thereto through the fixing of a set screw, coupled by means of a helical coupling so that, once the coupling is complete, the set screw is locked in the desired position and the corrective bar is fixed into the housing provided in the screw head. Therefore, until the set screw is correctly coupled, the head of the polyaxial screw is free to move.

In typical approaches, instruments are known for the coupling of a set screw with a head of a polyaxial screw. The fixing instruments can be likened to screwdrivers through which it is possible to act on the set screw to create the threaded coupling between it and the head of the polyaxial screw. In fact, through the coupling, the set screw drops into the head of the polyaxial screw until it presses against a corrective bar and stops against it. In this way, the corrective bar is controlled to press against the spherical end of the threaded stem of the polyaxial screw, which is also contained in the head of the screw. In this way, the spherical end of the stem of the polyaxial screw and the bar are locked in the desired position.

SUMMARY

Generally speaking, a fixing device is for a surgical anchor member. The fixing device may include a control component joined to a connecting portion, which is in turn connected to a shaft provided at one end with coupling units for connecting the fixing device to a fastening element suitable to couple with a respective fastening seat of a surgical anchor element. The fixing device may include a centering component for the coupling of the fastening member with the respective fastening seat of the surgical anchor member.

BRIEF DESCRIPTION OF THE DRAWINGS

FIG. 3 is a three-quarter view of the present invention;

FIG. 3a is a detailed view of detail A of FIG. 3,

FIG. 5a is a partial view of the fixing device for a surgical anchor member in coupling with a set screw;

FIG. 5b is a section according to line B-B in FIG. 5a;

FIG. 5c is a detailed view of detail C of FIG. 5b;

FIG. 10 is an overall view of the fixing device for a surgical anchor member in coupling with a polyaxial screw with the set screw decoupled whose head is inclined according to different angles;

DETAILED DESCRIPTION

Hence, it appears clear how it is necessary for the set screw to be located correctly within its housing provided in the head of the polyaxial screw, so as to guarantee the correct relative positioning of the bar with respect to the threaded stem of the polyaxial screw. Screwdrivers of the prior art, however, are not able to provide for the required functions satisfactorily and have some drawbacks.

A drawback of what is known in the state of the art is the possible off-axis insertion of the set screw with respect to the axis of the screw head in which the female screw thread is present. This incorrect insertion is not detected by the surgeon until a sticking phenomenon occurs, which stops the relative movement of the set screw with respect to the female screw thread of the polyaxial screw. The surgeon must then free the set screw and proceed to insert it again with the consequent wasted time and the possibility of misalignment of the polyaxial screw head with respect to its threaded stem.

Another drawback of what is known in the state of the art is the lack of alignment means for aligning the set screw with respect to the screw head so as to provide for the insertion of the set screw in a secure way. Another drawback of what is known in the state of the art is the need to operate manually on the screw head in order to achieve the perfect positioning of the corrective bar and to, still manually, maintain the chosen position for the screw head, during the set screw assembly operations.

The present invention, starting from the notion of these disadvantages, intends to provide a remedy for them. An object of the present invention is to provide a fixing device for a surgical anchor member able to guarantee the perfect automatic alignment between a set screw and a head of the anchoring device. Another object of the present invention is to provide a fixing device for a surgical anchor member able to allow a user to easily handle the device in situ, during the surgical operation, for the purpose of the correct fixing of the anchor member.

A further object of the present invention is to provide a device as specified that is able to allow the user to act on it using one hand only. Another object of the present invention is to provide a fixing device for a surgical anchor member able to be detachably coupled with the set screw, allowing its insertion into the screw head quickly, simply and easily. It will also be an object of the present invention to provide a device as illustrated in the following description that has a contained weight, reduced dimensions and is easy and comfortable to use.

Figure 1:
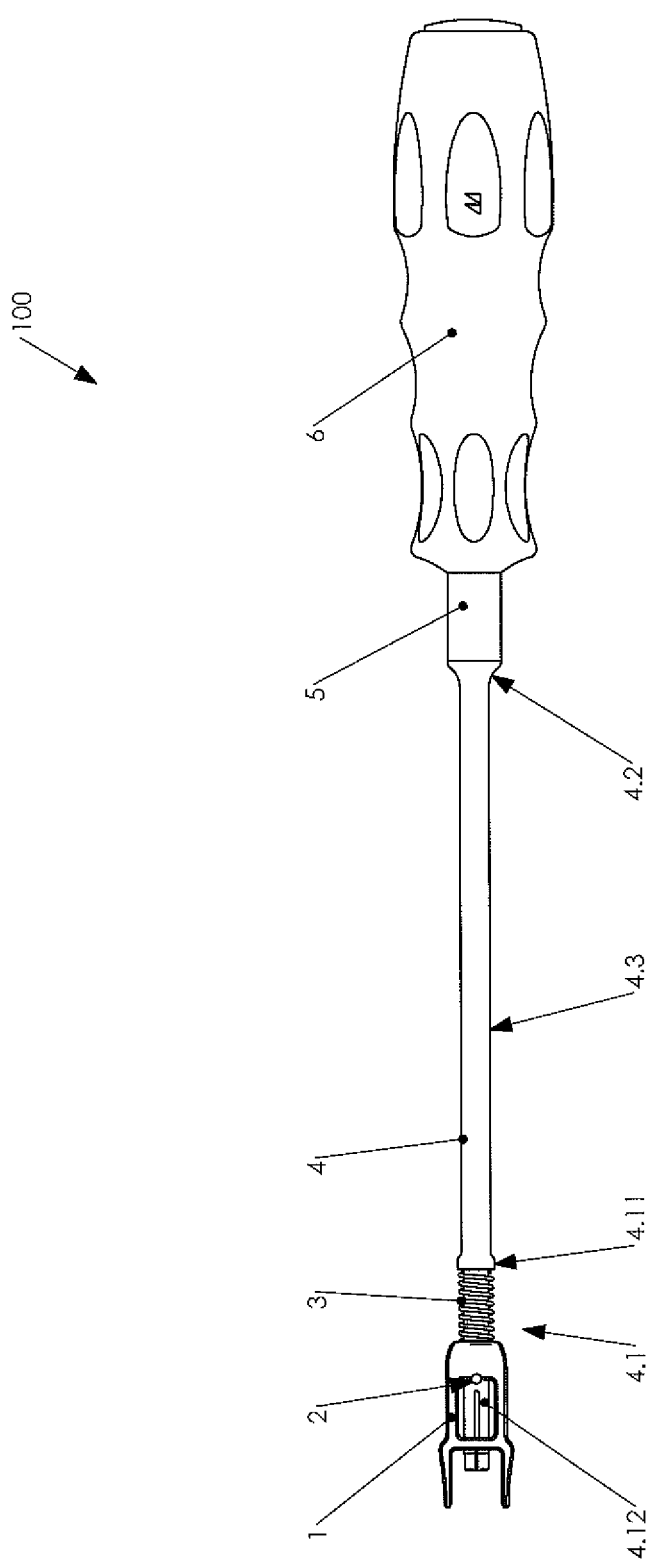
FIG. 1 is a view in front elevation of a fixing device for a surgical anchor member according to the present invention.
Figure 2:
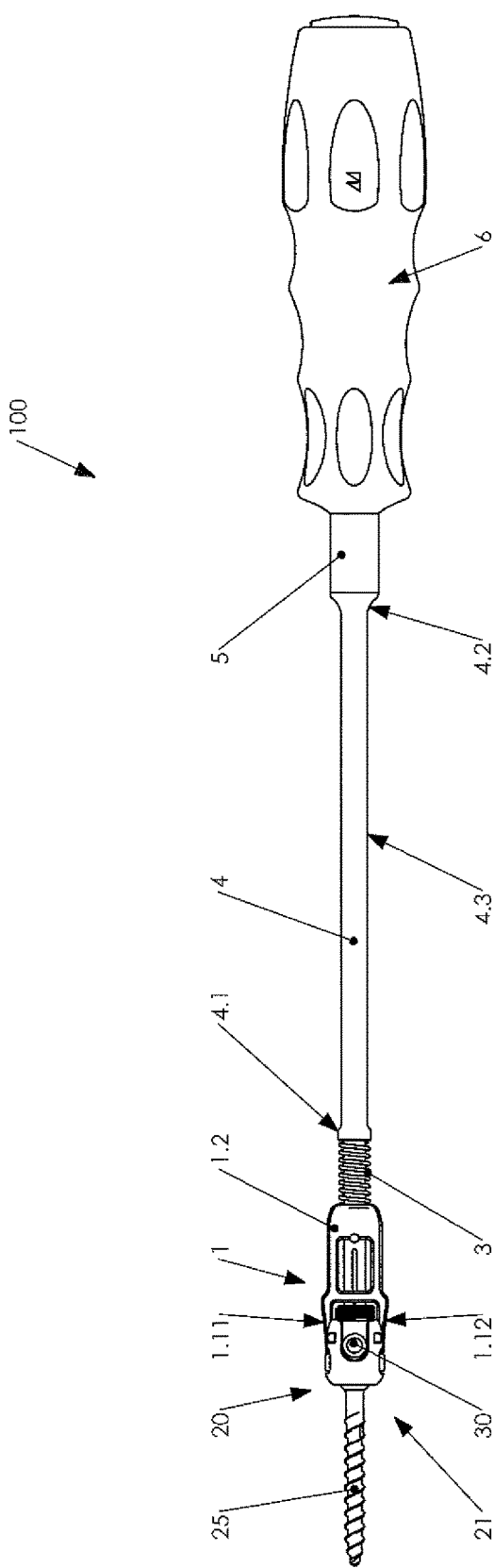
FIG. 2 is a view in front elevation of the fixing device for a surgical anchor member of FIG. 1 in coupling with a polyaxial screw.

In the drawing, 100 indicates the fixing device (i.e. a fixation device) for a surgical anchor member according to the present invention, as a whole. The fixing device 100 includes (FIG. 1): a control device 6, for example, a handle, coated in plastic/rubber material and having characteristic dimensions such as to make it easy and comfortable for the user to use; and a metal connecting portion 5, integral with the handle 6 and adapted to make the handle 6 solidly joined to a shaft 4, made of rigid material such as, for example, metal, metal alloys, polymeric and/or composite materials, having a circular section with a central area 4.3 with a constant section and a substantially cylindrical shape, an end 4.2 with a larger section and an end 4.1 with a variable section; an elastic means, for example, a spring 3, entirely fitted on to a part of the end 4.1 of the shaft 4 and engaged to strike a contact area 4.11 with a larger section than the end 4.1, on one of its sides proximal to the handle 6, and engaged to strike a centering means 1, for example, a fork, on one of its distal sides to the handle 6.

The fork 1 is fitted onto the free end portion 4.12 of the end 4.1. Integral with the free portion 4.12 and protruding from it, there is a stop means, for example, a pin 2 having a transversal axis with respect to the axis of the shaft 4. Furthermore, the free portion 4.12 has a through channel 4.13 (FIG. 4), extending for a substantial part of the free portion 4.12, U-shaped and such as to divide the free end portion 4.12 into two coupling units 4.14 and 4.15.

The fork 1 substantially has two parts: a first area, known as the engagement area 1.1 and a second area, known as the coupling area 1.2. This coupling area 1.2 has a substantially hollow circular section and is fitted and free to slide on the free end 4.1 of the shaft 4, interacting with the shaft 4 through the spring 3. In fact, the spring 3 is engaged, on one side, striking the back 1.21 of the coupling area 1.2 and on the other striking the increased section area 4.11 of the shaft 4. Thus, by keeping the fork 1 still and pressing on the handle 6, the spring 3 is compressed, bringing the free end 4.12 to slide freely into the fork 1, hence allowing a relative translation between the fork 1 and the shaft 4. By removing the pressure on the handle 6, the spring 3 regains its neutral position (also known as the rest position) and the position of the fork 1, in relation to the free end 4.12 of the shaft 4, returns to the initial one. It is to be noted that the spring 3 can be assembled on the end 4.1 of the shaft 4 in the pre-load configuration; however, for the purpose of the present description, the term "neutral position" or "rest position" will be used for the spring 3 which has no loads acting on it imposed by the user. On the coupling area 1.2 of the fork 1 and extending for a substantial part of it, there is an aperture 1.22, with a substantially rectangular shape and having, on its proximal side to the handle 6, a seat, for example, a notch 1.23, centered with respect to the axis of the shaft 4 and adapted to be engaged with the pin 2, when the spring 3 is in neutral position.

Figure 4:
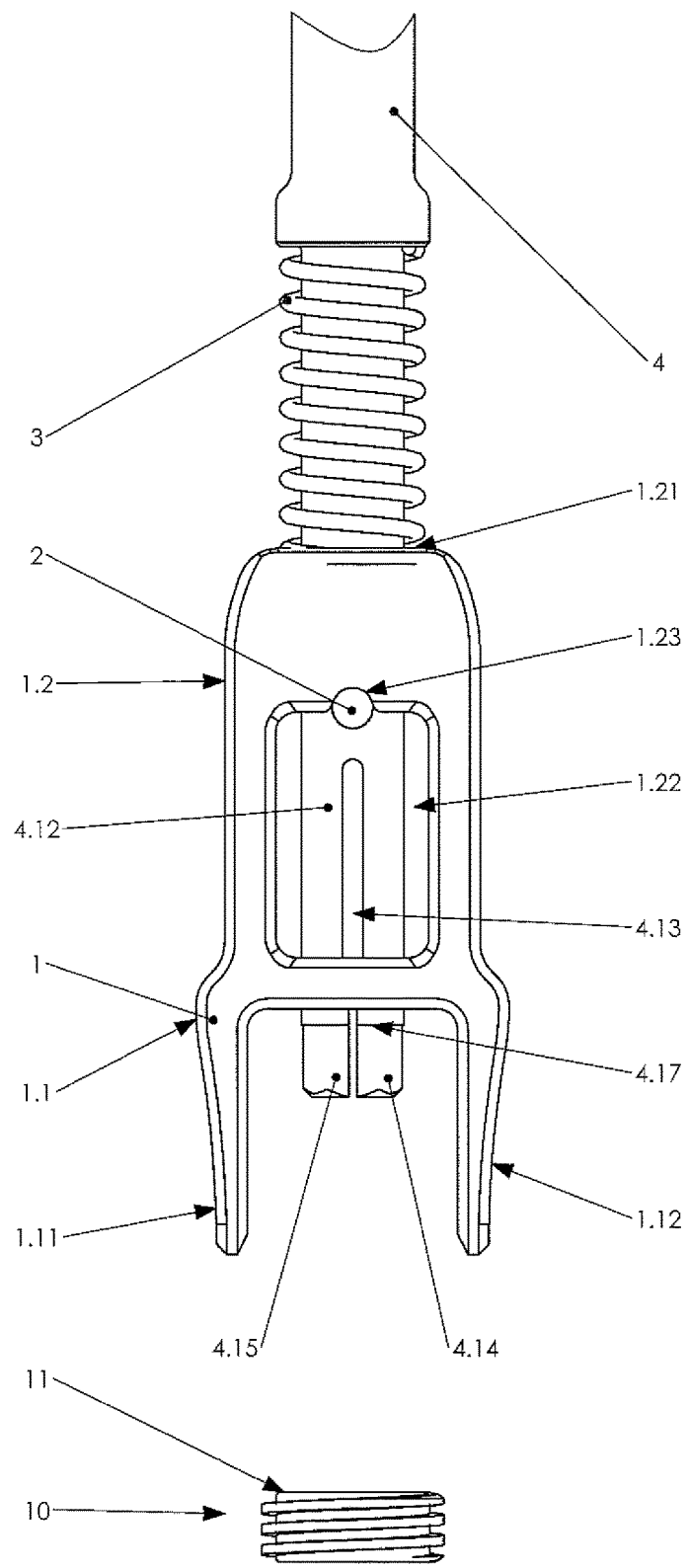
FIG. 4 is a side elevation view of the detail of FIG. 3a with the relative set screw decoupled.
Figure 6:
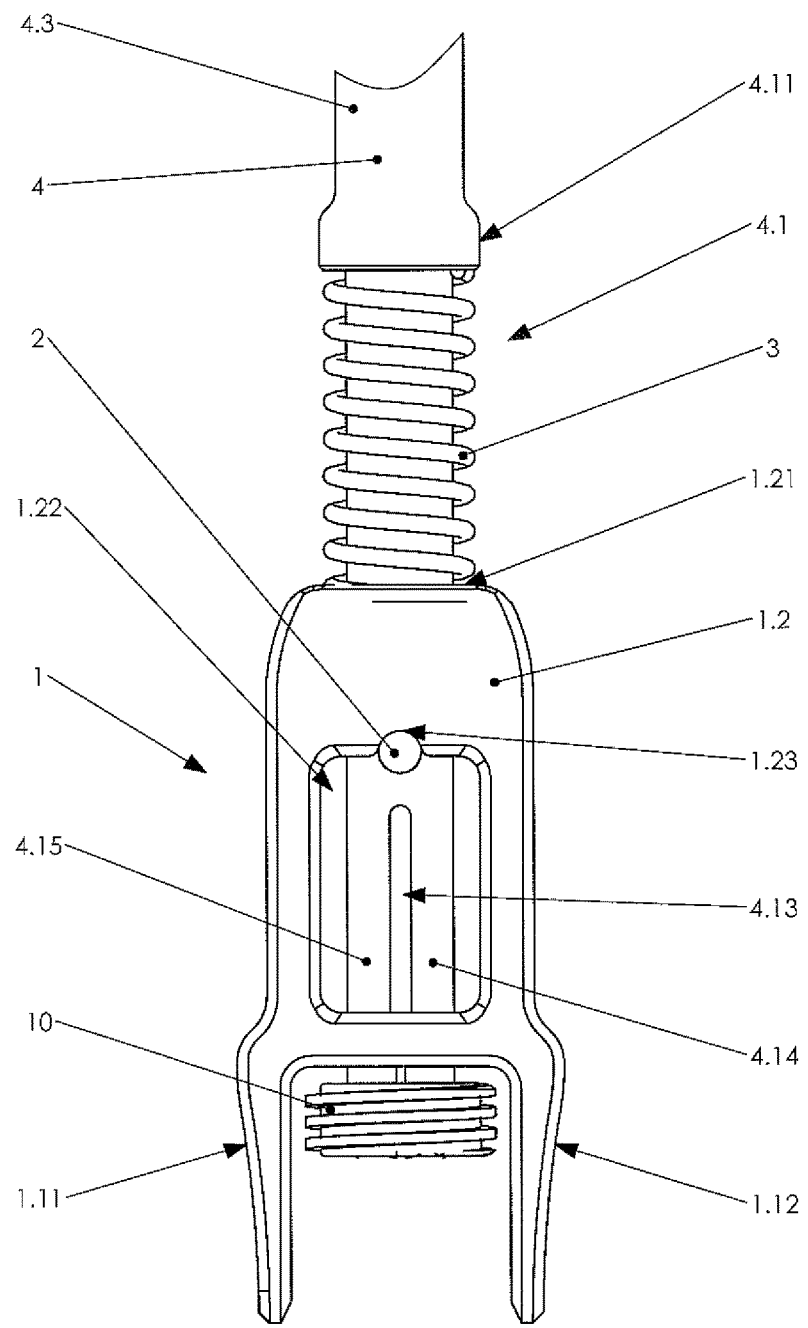
FIG. 6 is a view as per FIG. 4 but with the set screw coupled.
Figure 7:
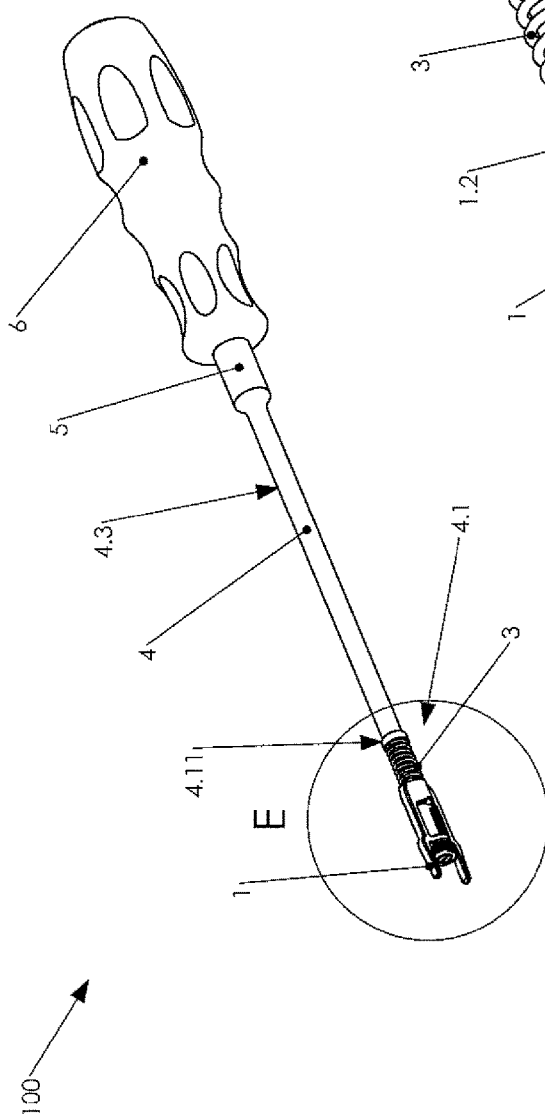
FIG. 7 is a three-quarter view of the device according to the present invention with the set screw coupled.
Figure 7A:
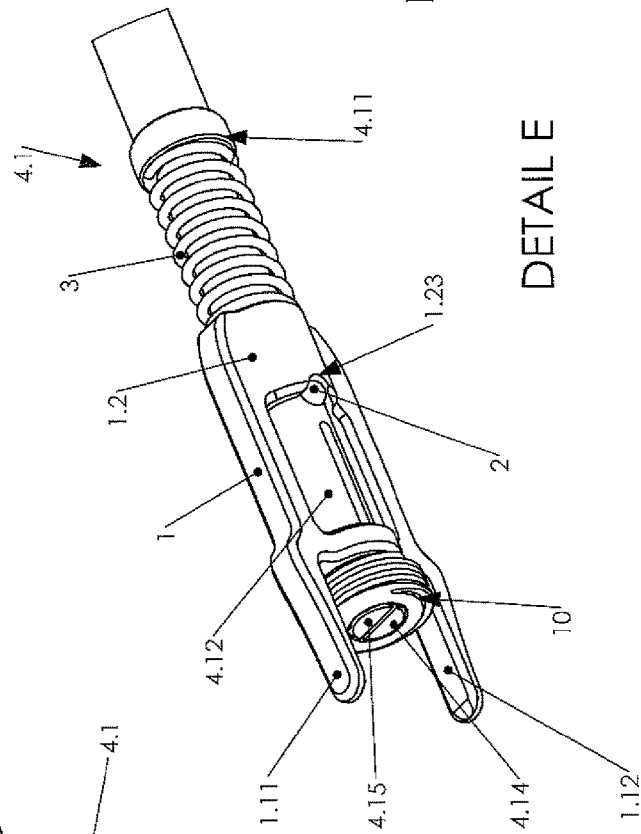
FIG. 7a is a detailed view of detail E of FIG. 7.

The engagement area 1.1 has two engagement means, for example, two prongs 1.11 and 1.12, having a tapered section towards the free ends and adapted to be coupled with a respective retaining area, for example, two centering grooves 22, provided in a fastening seat 21.1 of a head 21 of a surgical anchor member 20. Note that, between the two prongs 1.11 and 1.12, in a substantially centered position, the free end 4.12 of the shaft 4 protrudes. As mentioned, the free end 4.12 of the shaft 4 is split into two coupling units 4.14 and 4.15 by the through channel 4.13. The two coupling units 4.14 and 4.15 have a reduced section for a substantial part of the section protruding between the two prongs 1.11 and 1.12, so as to form an abutment 4.17 (FIG. 4).

Operation.

Figure 14:
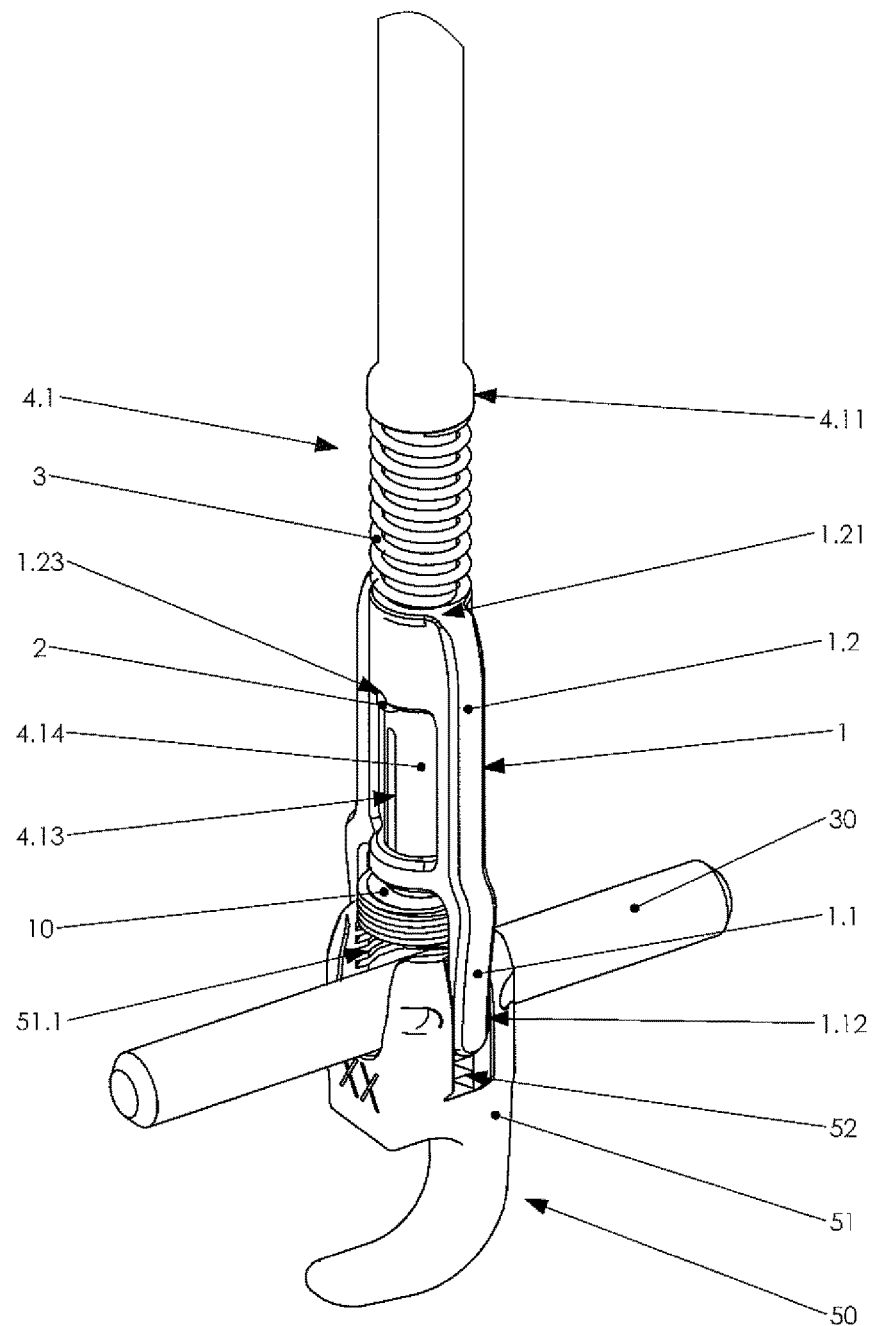
FIG. 14 illustrates the fixing device for a surgical anchor member in the coupled configuration with an anchoring hook.
Figure 15:
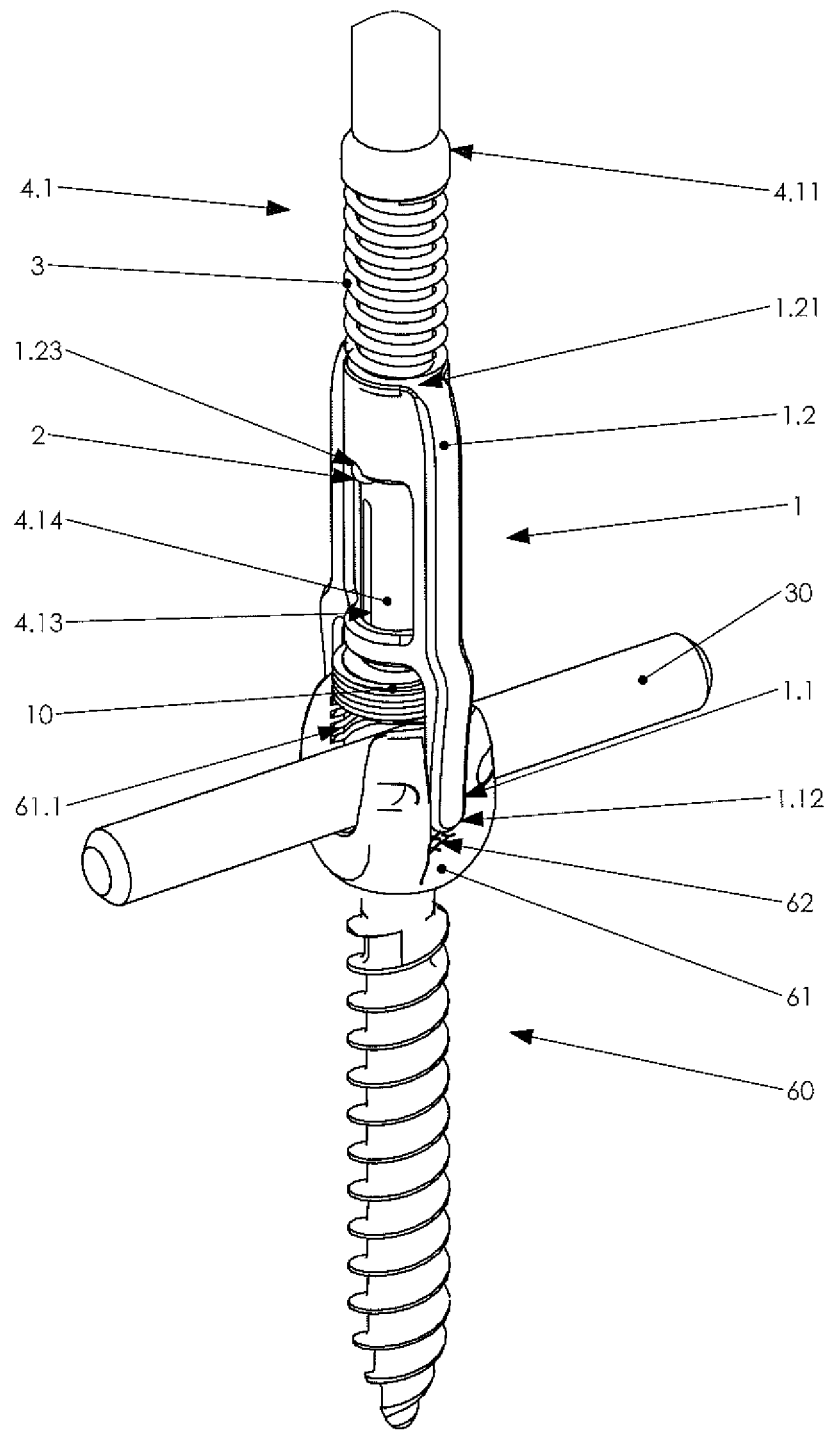
FIG. 15 illustrates the fixing device for a surgical anchor member in the coupled configuration with a monoaxial screw.
Figure 16:
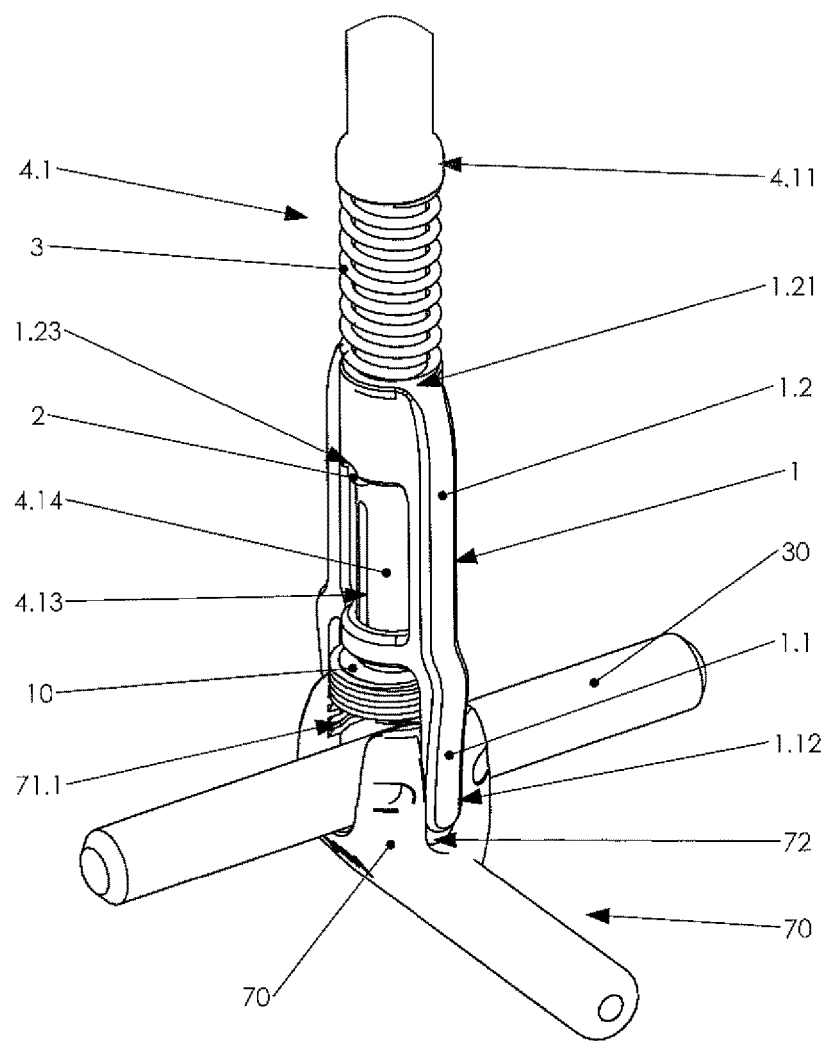
FIG. 16 illustrates the fixing device for a surgical anchor member in the coupled configuration with a lateral connector.

The fixing device 100 for a surgical anchor member 20 according to the present invention, as illustrated in the appended drawing purely by way of example, is configured for the coupling of a fastening element 10, for example, a set screw, within a fastening seat 21.1 of the head 21 of a surgical anchor member 20, for example, a polyaxial screw as illustrated in FIGS. from 8 to 13, an anchoring hook 50 as illustrated in FIG. 14, a monoaxial screw 60 as illustrated in FIG. 15, or a lateral connector 70 as illustrated in FIG. 16.

Gripping the fixing device 100 by the handle 6, the user positions the set screw 10 on a support surface (not shown) and the prongs 1.11 and 1.12 in proximity to the side of the set screw 10. By exerting pressure on the handle 6, through the rigid structure formed by the handle, the connecting portion 5, the shaft 4 and its increased section area 4.11, the spring is compressed and allows the relative translation of the free portion 4.12 of the end 4.1 of the shaft 4 with respect to the fork 1. The translation makes the two coupling units 4.14 and 4.15 be forced first against the upper part 11 of the set screw 10 and then to approach one another until they close the channel 4.13 and penetrate into the relevant blind coupling cavity (known and not illustrated) provided in the set screw 10, hence performing the solid coupling between the set screw 10 and the fixing device 100.

It is to be noted that the shape of the coupling units 4.14 and 4.15 is such that, once they are forced to touch one another closing the channel 4.13 as described above, they assume a complementary conformation to the blind coupling channel provided in the set screw 10, so as to be able to rotate integrally therewith. Please also note that the coupling units 4.14 and 4.15 penetrate into the blind cavity until the surface 11 of the set screw 10 strikes against the abutment 4.17. In this way, an optimal coupling between the two coupling units 4.14 and 4.15 and the set screw 10 is guaranteed, preventing the set screw 10 being able to return along the free end 4.12 during the helical coupling operations with the head of a surgical anchor member, for example, the head 21 of the polyaxial screw 20 as illustrated in FIGS. 8-13. Furthermore, the coupling provides a certain resistance to tensile strain aiming to separate the set screw 10 from the fixing device 100, without this making the voluntary decoupling of the set screw 10 from the fixing device 100 difficult.

Figure 8:
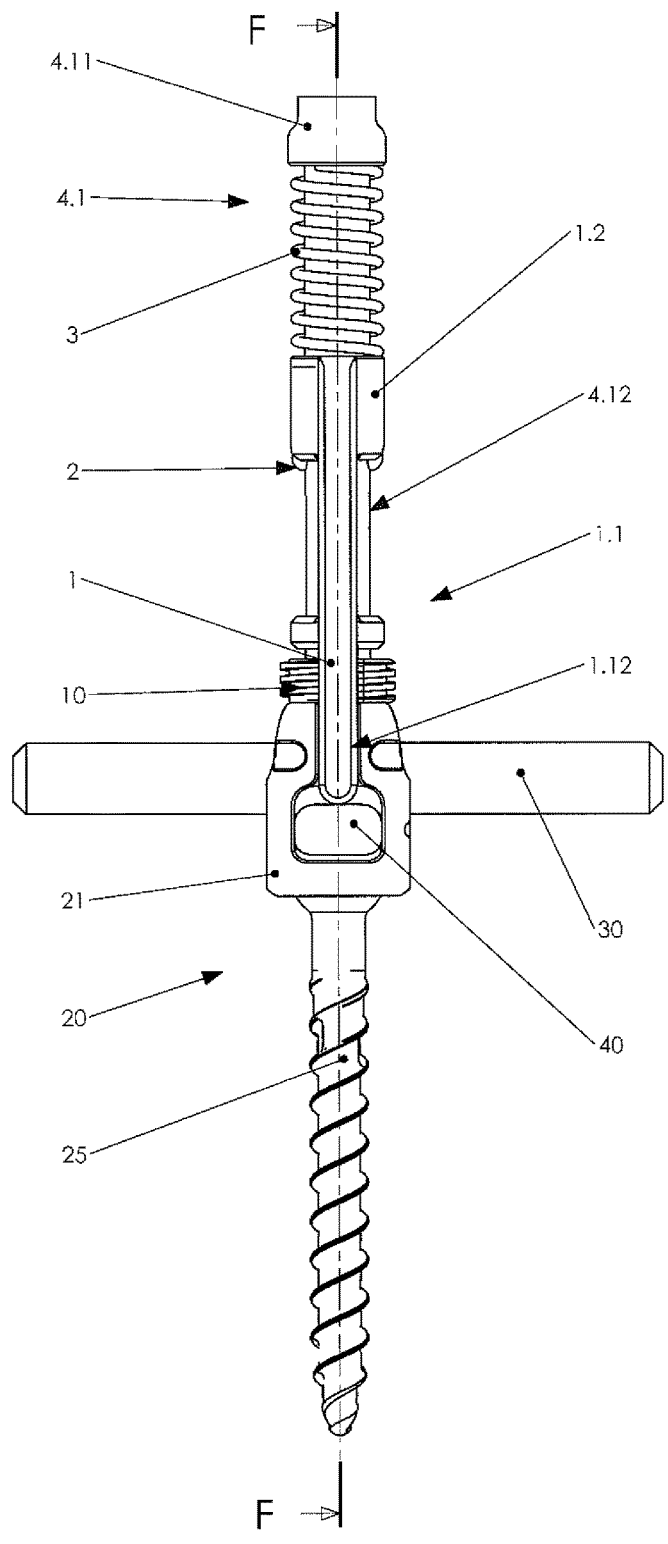
FIG. 8 is a partial side elevation view of the fixing device for a surgical anchor member in the coupling configuration with a polyaxial screw with the set screw uncoupled.
Figure 9:
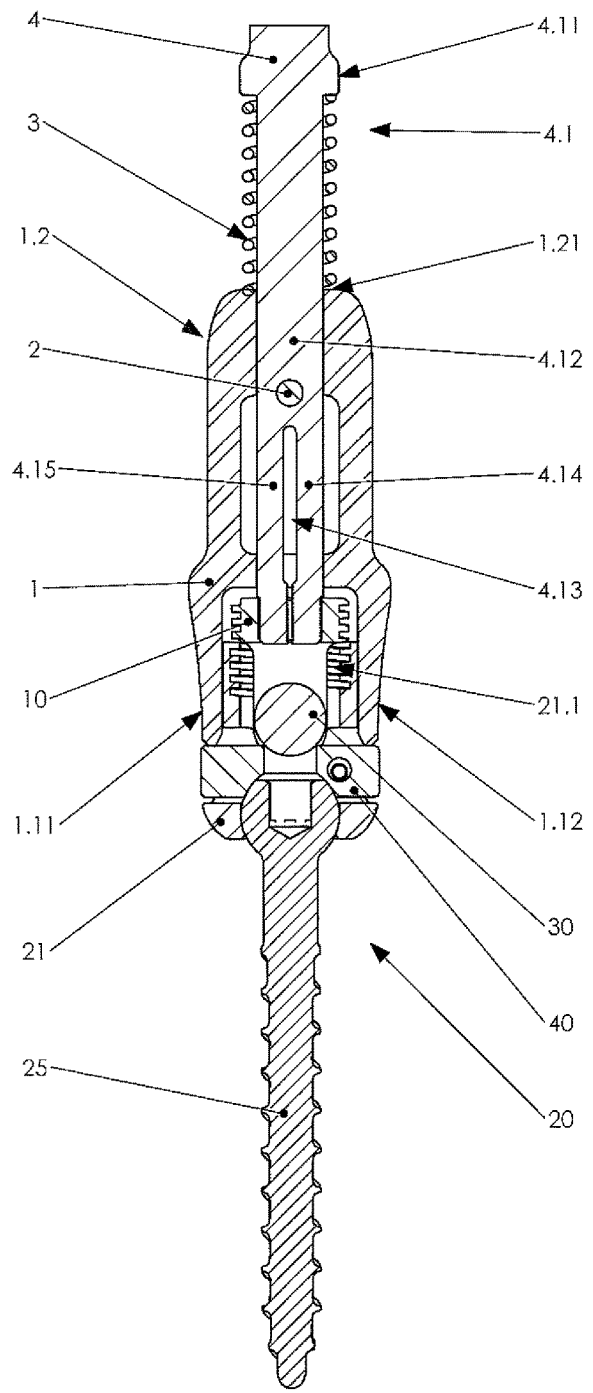
FIG. 9 is a sectional view according to line F-F in FIG. 8.
Figure 11:
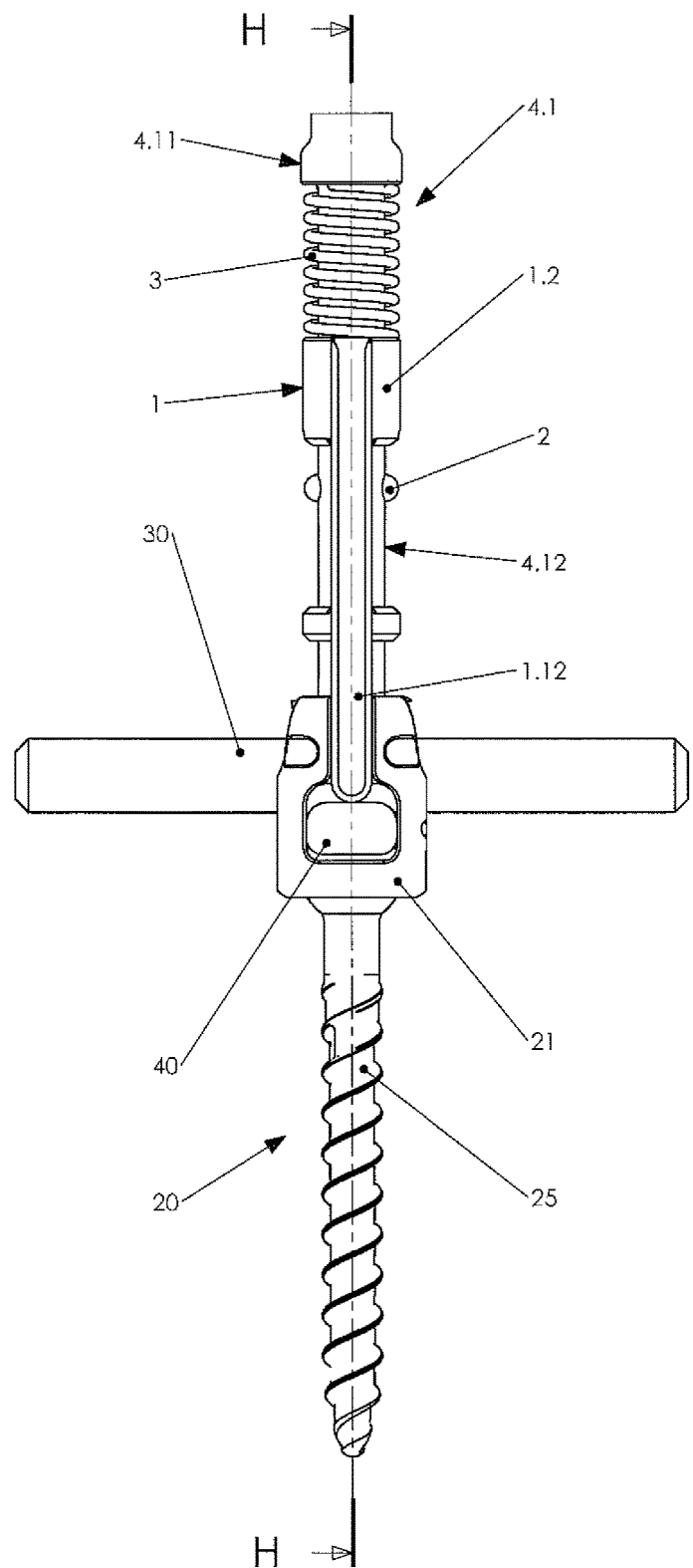
FIG. 11 is a partial side elevation view of the fixing device for a surgical anchor member in the coupled configuration with a polyaxial screw.
Figure 12:
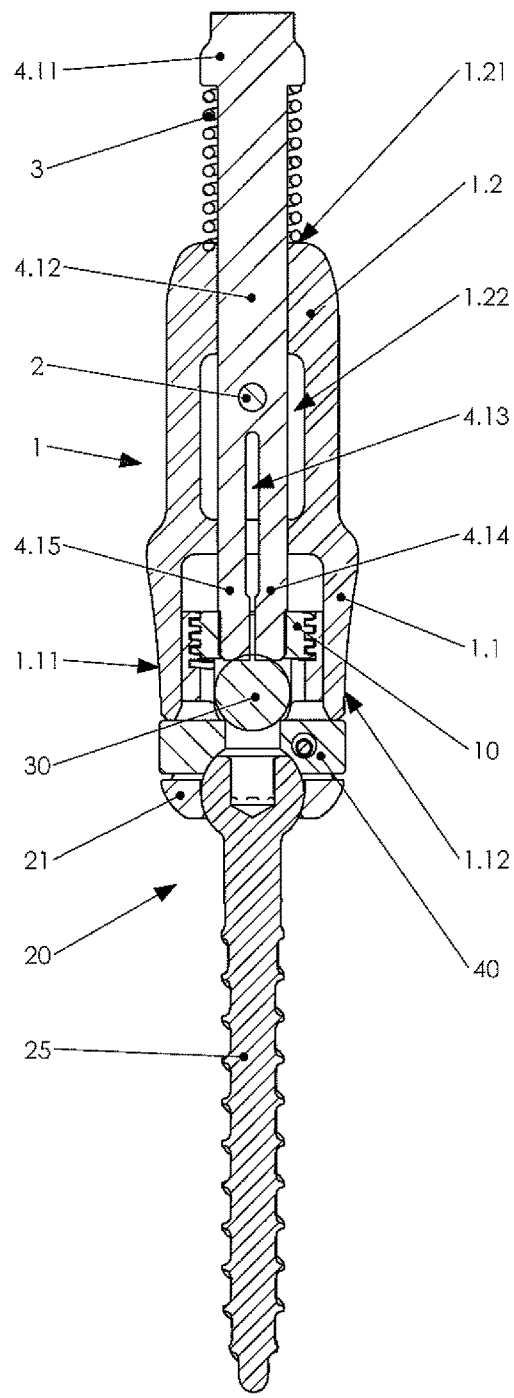
FIG. 12 is a sectional view according to line H-H in FIG. 11.
Figure 13:
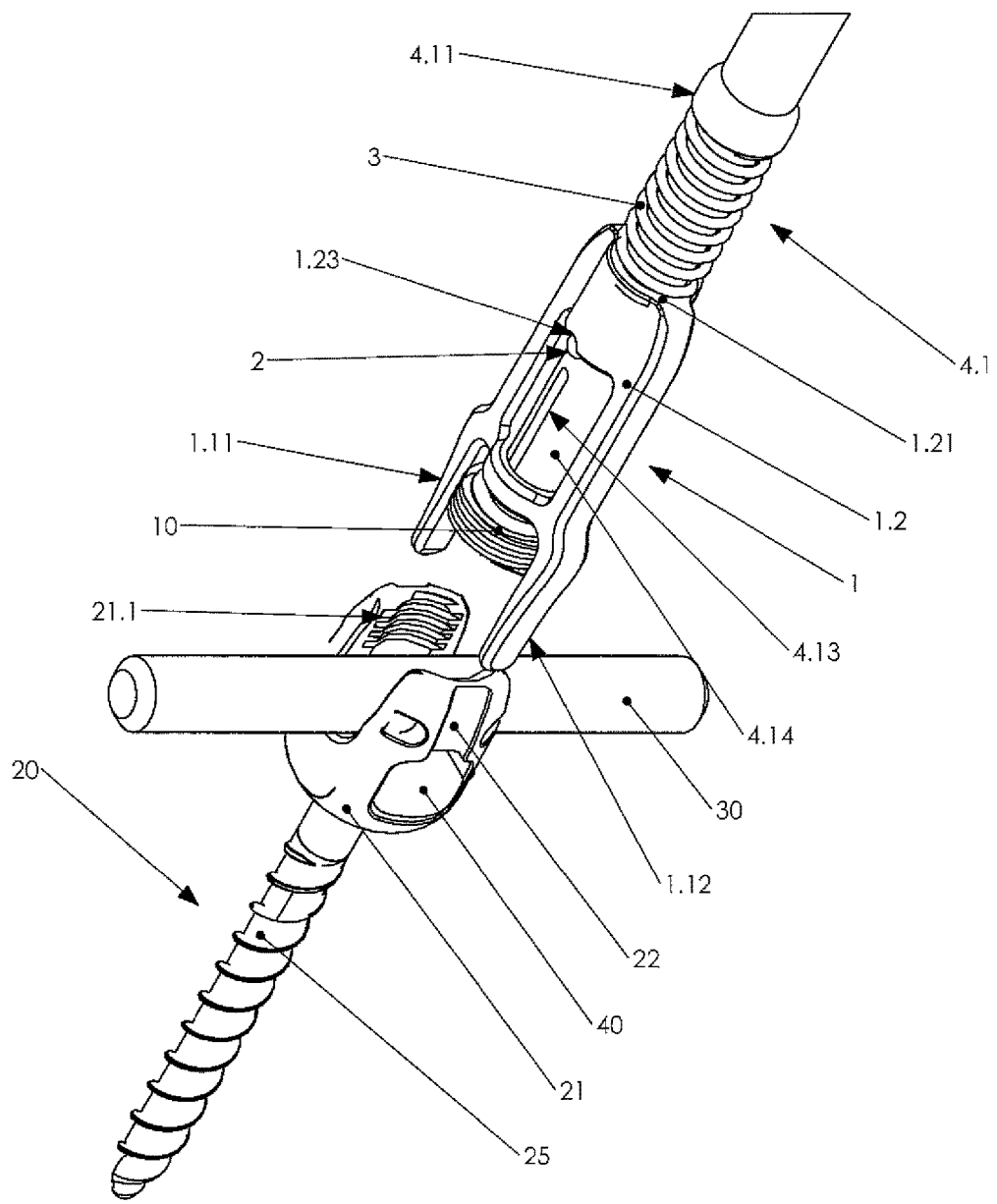
FIG. 13 is a partial three-quarter view of the fixing device for a surgical anchor member in the decoupled configuration with a polyaxial screw.

Once the coupling has been performed, as described above, it is possible to bring the two prongs 1.11 and 1.12 to engage the respective retaining areas, for example, the grooves 22, provided in the head 21 of the polyaxial screw 20, as illustrated in FIG. 8. This operation is facilitated by the presence of the pin 2 in the coupling position with the notch 1.23 of the aperture 1.22, when the spring 3 is in neutral position. In fact, when the pin is in the coupled position with the notch 1.23, it prevents, within certain limits, the fork 1 turning idly with respect to the free end 4.12, hence guaranteeing a quick and easy coupling of the prongs 1.11 and 1.12 with the respective grooves, for example, those envisaged on the head 21 of the surgical anchor member 20, in the reference figure, a polyaxial screw.

Advantageously, at this point, it is possible to act on the handle 6 of the fixing device 100 in order to choose the correct alignment of the head 21 of the polyaxial screw 20 with respect to its threaded stem 25, as illustrated in FIG. 10. This is possible thanks to the engagement of the notch 1.23 by the pin 2. In fact, when the spring 3 is in the neutral position, the pin 2, assembled transversally to the axis of the shaft 4 and solidly joined thereto, is engaged within the notch 1.23. This coupling ensures that the fork 1 is forced to rotate integrally with the shaft 4 when the torque imposed on the handle 6 by the user falls within certain limits, the limits being set by the shape of the notch 1.23.

Once the desired position has been reached, through pressure on the handle 6, the consequent compression of the spring 3 and relative translation of the end 4.12 with respect to the fork 1, the pin 2 is disengaged from the notch 1.23. At this point, thanks to a torque applied by the user on the handle 6, the shaft 4 can be rotated and, consequently, also its end 4.12 with which the set screw 10 is integral, while the fork 1 remains coupled to the head 21 of the polyaxial screw 20 without rotating. In this way, thanks to the rotation, the set screw 10 is coupled in the fastening seat 21.1 of the head 21 of the polyaxial screw 20 until the head 21 of the polyaxial screw 20 is fixed in the desired position with respect to the stem 25 of the polyaxial screw 20 and the consequent locking of the set formed by the corrective bar 30 and the insert 40.

It is clear from the above that the presence of the prongs 1.11 and 1.12 in coupling with the grooves, for example, those provided on the head 21 of the polyaxial screw 20, guarantee the perfect alignment between the set screws 10 and the head 21 of the surgical anchor member, for example, the polyaxial screw 20, preventing sticking phenomena between the thread of the set screw 10 and the relative female screw thread provided in the fastening seat 21.1 of the head 21 of the polyaxial screw 20.

It is easy to understand, for a person skilled in the art, how the present invention could be functional to the coupling of a set screw 10, potentially with a different shape from that illustrated in the drawings appended hereto, purely by way of non-limiting example, but with similar functions, with other types of anchor members used in surgical practice. Some brief descriptions follow of possible uses of the present invention in combination with anchor members typically used in the surgical field. Where not specified otherwise, all the advantageous characteristics described above illustrating the preferred embodiment remain valid also for the variations to the uses illustrated below.

An example of the use of the present invention with an anchor member of a different type with respect to what is described above is illustrated in FIG. 15. In the FIG. 15, instead of a polyaxial screw 20, as illustrated in FIGS. 2 and 8-13, the fixing device 100 is used in cooperation with a monoaxial screw 60. In this case, the alignment function of the head 61 of the monoaxial screw 60 with its threaded stem is not required, since the monoaxial screw 60 has a fixed head 61. However, the presence of prongs 1.11 and 1.12 received in the retaining areas 62 provided in the head 61 of the monoaxial screw 60 allow the perfect positioning of the set screw 10 with respect to its respective seat 61.1 provided in the head 61 of the monoaxial screw 60, guaranteeing the correct fastening of the bar 30 to the monoaxial screw 60.

Another example of the use of the fixing device 100 according to the present invention is illustrated in FIG. 14. In the FIG. 14, the fixing device 100 is used for the threaded coupling between a set screw 10 and another anchor member 50, for example, an anchoring hook. The anchoring hook 50 has a fastening seat 51.1, internally threaded, in the head 51 of the anchoring hook 50. Also in this case, there are retaining areas 52, provided on the head 51 of the anchoring hook 50 adapted to receive the prongs 1.11 and 1.12 of the fixing device. As described for the preceding methods of use, the use of prongs 1.11 and 1.12 of the respective retaining areas 52 creates the perfect alignment between the set screw 10 and the head 51 of the anchoring hook 50, allowing the correct placement of the set screw 10 and implementing the fastening of the bar 30 solidly to the anchoring hook 50.

Finally, a further use of the fixing device 100 according to the present invention is illustrated in FIG. 16. In the FIG. 16, a further anchor member 70 is illustrated, for example, a lateral connector, able to be anchored to a second anchor member, for example, a polyaxial screw like those described above (not illustrated), and able to receive a bar 30 in a housing 71.1 within its head 71. Also in this case, the head 71 of the anchor member 70 is adapted to house a set screw 10 and has retaining areas 72 adapted to receive prongs 1.11 and 1.12 of the fixing device 100. As described above, the coupling of the prongs 1.11 and 1.12 with the respective retaining areas 72 makes the perfect alignment between the set screw 10 and the head 71 of the lateral connector 70 possible so as to make the threaded coupling between the set screw 10 and the head 71 of the anchor member 70 secure, quick and simple. By creating this coupling the bar 30 is locked in the desired position within the head 71.

As appears clearly from the above description, the present invention advantageously achieves the objects described above. Naturally, numerous variants can be made to what is described and illustrated merely by way of non-limiting example, without for this reason departing from the protective scope of the present invention and therefore from the domain of the present industrial patent.

The invention claimed is:

1. A fixing device for a surgical anchor member comprising:
    control means joined to a connecting portion which is in turn connected to a shaft provided at one end with coupling units for connecting said fixing device to a fastening element suitable to couple with a respective fastening seat of a surgical anchor element;
    centering means for the coupling of said fastening member with the respective fastening seat of the surgical anchor member, wherein said centering means comprises an aperture suitable to receive a stop means; and
    a stop means located in the aperture of the centering means, wherein said stop means has two modes of operation: engaged and disengaged, wherein, when in the engaged mode, the centering means rotates with a rotation of the shaft and wherein, when in the disengaged mode, the centering means does not rotate with a rotation of the shaft.

2. The fixing device for a surgical anchor member as claimed in claim 1, wherein said centering means comprise at least a fork coupled to one end of the shaft.

3. The fixing device for a surgical anchor member as claimed in claim 1, wherein said centering means comprise an engagement area provided with at least one engagement means suitable to be received within a respective retaining area of the surgical anchor member.

4. The fixing device for a surgical anchor member as claimed in claim 2, wherein said engagement area protrudes at least partially from one end of the shaft.

5. The fixing device for a surgical anchor member as claimed in claim 1, wherein an elastic means can be compressed via the shaft.

6. The fixing device for a surgical anchor member as claimed in claim 5, wherein said elastic means is arranged between said centering means and a contact area of the shaft so as to permit a relative motion between said centering means and said shaft upon deformation of the elastic means.

7. The fixing device for a surgical anchor member as claimed in claim 1, wherein said stop means is integrally joined to and at least partially protruding from the shaft.

8. The fixing device for a surgical anchor member as claimed in claim 1, wherein said aperture comprises a seat wherein the stop means is at least partially received when the elastic means is in the rest configuration and is capable of releasing itself from said seat when said elastic element is deformed.

9. The fixing device for a surgical anchor member as claimed in claim 1, wherein a free portion of the shaft comprises a channel shaped so as to divide said free portion into two coupling units capable of coupling with respective seats provided in the fixing device.

10. The fixing device for
    a surgical anchor member as claimed in claim 2, wherein the centering means comprise at least one engagement member.

11. The fixing device for a surgical anchor member as claimed in claim 10, wherein said at least one engagement member of said centering means is suitable for coupling with a relative retaining area provided in a surgical anchor member, said at least one engagement member and said relative retaining area being configured so that said centering means and said retaining area of a surgical anchor member act as a single body with respect to a roto-translational force.

* * * * *